United States Patent
Jung et al.

(10) Patent No.: US 9,809,634 B2
(45) Date of Patent: Nov. 7, 2017

(54) COMPOSITION COMPRISING BRANCHED MULTIPEPTIDE VACCINE AND VACCINE COMPRISING THE SAME

(71) Applicant: INDUSTRY FOUNDATION OF CHONNAM NATIONAL UNIVERSITY, Gwangju (KR)

(72) Inventors: Tae-Young Jung, Gwangju (KR); Young-Hee Kim, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 31 days.

(21) Appl. No.: 14/985,660

(22) Filed: Dec. 31, 2015

(65) Prior Publication Data

US 2017/0037154 A1    Feb. 9, 2017

(30) Foreign Application Priority Data

Aug. 4, 2015  (KR) .................. 10-2015-0109936

(51) Int. Cl.
| | |
|---|---|
| *C07K 14/47* | (2006.01) |
| *C07K 7/06* | (2006.01) |
| *C07K 14/705* | (2006.01) |
| *C07K 14/445* | (2006.01) |
| *A61K 39/00* | (2006.01) |

(52) U.S. Cl.
CPC ...... *C07K 14/4747* (2013.01); *A61K 39/0011* (2013.01); *C07K 7/06* (2013.01); *C07K 14/445* (2013.01); *C07K 14/4703* (2013.01); *C07K 14/4748* (2013.01); *C07K 14/70596* (2013.01); *A61K 2039/627* (2013.01); *A61K 2039/645* (2013.01); *A61K 2039/70* (2013.01); *C07K 2319/00* (2013.01)

(58) Field of Classification Search
None
See application file for complete search history.

(56) References Cited

U.S. PATENT DOCUMENTS

2004/0210035 A1 * 10/2004 Straten ............... C07K 14/4738
530/350
2009/0017000 A1 *  1/2009 Cai .................... A61K 39/0011
424/93.71

OTHER PUBLICATIONS

Autio 2011 "mini-peg spacering of VAP-1 targeting 68ga-dotavap-p1 peptide improves pet imaging of inflammation" ejnmmi research 1:10.*
Ciesielski 2005 "cellular antitumor immune response to a branched lysine multiple antigenic peptide containing epitopes of a common tumor-specific antigen in a rat glioma" Cancer Immunol Immunother 54:107-119.*
Uniprot 2017 "P14209 (CD99_Human)" accessed from uniprot.org on Mar. 22, 2017.*
Wang 2011 "multiple antigenic peptides of human heparanase elicit a much more potent immune response against tumors" Cancer Prev Research 4(8):1285-1295.*
"14th Asian Australian Congress of Neurological Surgeons," Final Program Book, Presentation dates: Apr. 15-18, 2015, Presented by: Young-Hee Kim, 3 pages.
Tae-Young Jung et al., "Immunological Characterization of Glioblastoma Cells for Immunotherapy," Anticancer Research, 2013, pp. 2525-2534, vol. 33.
Valerie Dutoit et al., "Exploiting the glioblastoma peptidome to discover novel tumour-associated antigens for immunotherapy," BRAIN, Mar. 14, 2012, pp. 1042-1054, vol. 135.
Korean Intellectual Property Office: Communication dated Mar. 8, 2017 in counterpart application No. 10-2015-0109936.
Patricia Antunes et al. "Influence of Different Spacers on the Biological Profile of a DOTA—Somatostatin Analogue" Bioconjugate Chem. 2007, vol. 18, No. 1 (pp. 84-92).

* cited by examiner

*Primary Examiner* — Adam M Weidner
(74) *Attorney, Agent, or Firm* — Sughrue Mion, PLLC (57) ABSTRACT

Provided are a branched multi-peptide composition and a vaccine including the same. The branched multi-peptide vaccine according to the present invention is easy to be produced and utilized, thereby being easily applied to the treatment, and is capable of maintaining stable reaction in vivo, such that it is expected that the branched multi-peptide vaccine according to the present invention acts as an effective vaccine. Further, for the tumor antigen peptide, the present invention may select an antigen that is largely expressed in a malignant brain tumor. In addition, from now on, it is expected that tumor antigens having a large expression level may be analyzed depending on tumor characteristics of an individual patient, such that the branched multi-peptide vaccine according to the present invention may be utilized for producing personalized branched peptides and vaccines using the same.

3 Claims, 8 Drawing Sheets

SEQUENCE LISTING

```
<160> NUMBER OF SEQ ID NOS: 17

<210> SEQ ID NO 1
<211> LENGTH: 9
<212> TYPE: PRT
<213> ORGANISM: Artificial Sequence
<220> FEATURE:
<223> OTHER INFORMATION: Peptide ERBB2-369

<400> SEQUENCE: 1

Lys Ile Phe Gly Ser Leu Ala Phe Leu
 1               5

<210> SEQ ID NO 2
<211> LENGTH: 9
<212> TYPE: PRT
<213> ORGANISM: Artificial Sequence
<220> FEATURE:
<223> OTHER INFORMATION: Peptide ERBB2-106

<400> SEQUENCE: 2

Gln Leu Phe Glu Asp Asn Tyr Ala Leu
 1               5

<210> SEQ ID NO 3
<211> LENGTH: 10
<212> TYPE: PRT
<213> ORGANISM: Artificial Sequence
<220> FEATURE:
<223> OTHER INFORMATION: Peptide ERBB2-689

<400> SEQUENCE: 3

Arg Leu Leu Gln Glu Thr Thr Glu Leu Val
 1               5                   10

<210> SEQ ID NO 4
<211> LENGTH: 9
```

```
<212> TYPE: PRT
<213> ORGANISM: Artificial Sequence
<220> FEATURE:
<223> OTHER INFORMATION: Peptide ERBB2-789

<400> SEQUENCE: 4

Cys Leu Thr Ser Thr Val Gln Leu Val
 1               5

<210> SEQ ID NO 5
<211> LENGTH: 9
<212> TYPE: PRT
<213> ORGANISM: Artificial Sequence
<220> FEATURE:
<223> OTHER INFORMATION: Peptide ERBB2-63

<400> SEQUENCE: 5

Thr Tyr Leu Pro Thr Asn Ala Ser Leu
 1               5

<210> SEQ ID NO 6
<211> LENGTH: 10
<212> TYPE: PRT
<213> ORGANISM: Artificial Sequence
<220> FEATURE:
<223> OTHER INFORMATION: Peptide BIRC5-5

<400> SEQUENCE: 6

Thr Leu Pro Pro Ala Trp Gln Pro Glu Leu
 1               5                  10

<210> SEQ ID NO 7
<211> LENGTH: 9
<212> TYPE: PRT
<213> ORGANISM: Artificial Sequence
<220> FEATURE:
<223> OTHER INFORMATION: Peptide BIRC5-95

<400> SEQUENCE: 7

Glu Leu Thr Gly Glu Phe Leu Lys Leu
 1               5

<210> SEQ ID NO 8
<211> LENGTH: 9
<212> TYPE: PRT
<213> ORGANISM: Artificial Sequence
<220> FEATURE:
<223> OTHER INFORMATION: Peptide BIRC5-96 leucine

<400> SEQUENCE: 8

Leu Leu Leu Gly Glu Phe Leu Lys Leu
 1               5

<210> SEQ ID NO 9
<211> LENGTH: 9
<212> TYPE: PRT
<213> ORGANISM: Artificial Sequence
<220> FEATURE:
<223> OTHER INFORMATION: Peptide BIRC5-96 methionine

<400> SEQUENCE: 9

Leu Met Leu Gly Glu Phe Leu Lys Leu
 1               5

<210> SEQ ID NO 10
<211> LENGTH: 9
<212> TYPE: PRT
```

```
<213> ORGANISM: Artificial Sequence
<220> FEATURE:
<223> OTHER INFORMATION: Peptide CD99-9

<400> SEQUENCE: 10

Leu Leu Leu Phe Gly Leu Leu Gly Val
 1               5

<210> SEQ ID NO 11
<211> LENGTH: 9
<212> TYPE: PRT
<213> ORGANISM: Artificial Sequence
<220> FEATURE:
<223> OTHER INFORMATION: Peptide CD99-6

<400> SEQUENCE: 11

Ala Leu Ala Leu Leu Leu Phe Gly Leu
 1               5

<210> SEQ ID NO 12
<211> LENGTH: 9
<212> TYPE: PRT
<213> ORGANISM: Artificial Sequence
<220> FEATURE:
<223> OTHER INFORMATION: Peptide CD99-13

<400> SEQUENCE: 12

Gly Leu Leu Gly Val Leu Val Ala Ala
 1               5

<210> SEQ ID NO 13
<211> LENGTH: 9
<212> TYPE: PRT
<213> ORGANISM: Artificial Sequence
<220> FEATURE:
<223> OTHER INFORMATION: Peptide CD99-10

<400> SEQUENCE: 13

Leu Leu Phe Gly Leu Leu Gly Val Leu
 1               5

<210> SEQ ID NO 14
<211> LENGTH: 9
<212> TYPE: PRT
<213> ORGANISM: Artificial Sequence
<220> FEATURE:
<223> OTHER INFORMATION: Peptide WT1-126

<400> SEQUENCE: 14

Arg Met Phe Pro Asn Ala Pro Tyr Leu
 1               5

<210> SEQ ID NO 15
<211> LENGTH: 9
<212> TYPE: PRT
<213> ORGANISM: Artificial Sequence
<220> FEATURE:
<223> OTHER INFORMATION: Peptide WT1-235

<400> SEQUENCE: 15

Cys Tyr Thr Trp Asn Gln Met Asn Leu
 1               5

<210> SEQ ID NO 16
<211> LENGTH: 9
<212> TYPE: PRT
<213> ORGANISM: Artificial Sequence
```

```
<220> FEATURE:
<223> OTHER INFORMATION: Peptide WT1-235 modified

<400> SEQUENCE: 16

Cys Tyr Thr Trp Asn Gln Met Asn Leu
 1               5

<210> SEQ ID NO 17
<211> LENGTH: 15
<212> TYPE: PRT
<213> ORGANISM: Artificial Sequence
<220> FEATURE:
<223> OTHER INFORMATION: PanDR epitope
<220> FEATURE:
<221> NAME/KEY: VARIANT
<222> LOCATION: (3)
<223> OTHER INFORMATION: Xaa = cyclohexylalanine

<400> SEQUENCE: 17

Ala Lys Xaa Val Ala Ala Trp Thr Leu Lys Ala Ala Ala Glx Cys
 1               5                  10                  15
```

COMPOSITION COMPRISING BRANCHED MULTIPEPTIDE VACCINE AND VACCINE COMPRISING THE SAME

CROSS-REFERENCE TO RELATED APPLICATIONS

This application claims priority under 35 U.S.C. §119 to Korean Patent Application No. 10-2015-0109936, filed on Aug. 4, 2015, in the Korean Intellectual Property Office, the disclosure of which is incorporated herein by reference in its entirety.

TECHNICAL FIELD

The following disclosure relates to a branched multi-peptide composition and a vaccine including the same, and more particularly, to a branched multi-peptide composition including a tumor antigen peptide and a vaccine for cancer immunotherapy including the same.

BACKGROUND

The annual incidence of brain tumor is 5 to 15.8 per 100,000 people, which is lower than other cancers. However, due to the population aging, development of cancer diagnosis, and an increase in health benefits, the rate of brain cancer is still gradually increasing. Among the brain tumors, incurable malignant brain tumors easily recur to have a low survival rate even though various treatments such as surgery, chemotherapy, radiation therapy, etc., are performed. Among the malignant brain tumors, a glioblastoma consumes a large amount of time and cost in the initial treatment with standard therapy concurrently performing surgery, radiation therapy and chemotherapy; however, an average life span is merely 15 months due to recurrence. Accordingly, development into novel therapy to compensate for the radiation standard therapy has been urgently demanded. However, a new drug treatment of which effects have not been proven yet, increases economic burden of patients due to high costs.

In order to overcome the above-described limitations of the general methods used in cancer therapy, various treatments have been researched. Among them, cancer immunotherapy having cancer-specific treatment effects and no side effects, has recently received attention. Immunotherapy using dendritic cells or natural killer cells among cancer immunotherapy requires a large amount of time and costs to reach a practical step. However, a peptide vaccine may be simply produced at a low cost, may have low toxicity, and may be produced by combining various tumor antigens even though the peptide vaccine has a slightly deteriorated efficiency as compared to the immunotherapy using dendritic cells or natural killer cells. One example of producing a multi-peptide by using tumor antigens variously expressed in the malignant brain tumor, and performing clinical trials for the produced multi-peptide, is also known (Dutoit et al., 2012).

RELATED ART DOCUMENT (Patent Document 1) Dutoit V. et al., Brain 135:1042-1054, 2012.
(Patent Document 2) Jung T. Y. et al., Anticancer Research 33:2525-2534, 2013.

SUMMARY

An embodiment of the present invention is directed to providing a branched multi-peptide composition capable of having lasting effects in vivo by synthesizing and using various tumor antigens to overcome tumor cell heterogeneity of a malignant brain tumor, and a vaccine including the same.

In one general aspect, there is provided a multi-peptide composition for cancer immunotherapy, represented by Chemical Formula I below:

[Chemical Formula I]

in Chemical Formula I,
each of A, B and C is a subsequence residue of any one peptide selected from the group consisting of brain tumor antigens: CD99, BIRC5, ERBB2, WT-1 and PanDR epitope;
Sp is a spacer that links the subsequence residue to lysine; and
Lys is lysine.

Each of A, B and C may have any one amino acid sequence selected from SEQ ID NOs: 1 to 17. Preferably, A may have any one amino acid sequence selected from SEQ ID NOs: 1 to 5, B may have any one amino acid sequence selected from SEQ ID NOs: 6 to 9, and C may have any one amino acid sequence selected from SEQ ID NOs: 10 to 13. More preferably, A may have an amino acid sequence of SEQ ID NO: 1, B may have an amino acid sequence of SEQ ID NO: 9, and C may have an amino acid sequence of SEQ ID NO: 10.

In the present invention, Sp is a spacer, and is not limited, but may be 8-amino-3,6-dioxa-octanoic acid (mini-PEG2).

In another general aspect, there is provided a vaccine for cancer immunotherapy including the multi-peptide composition as described above.

Interferon, which is the first discovered cytokine, was identified as a material having an antiviral activity in the early days. Presently, the interferon is identified as a glycoprotein having immunomodulatory action, cell proliferation inhibitory action, etc., in addition to the antiviral activity. An important mechanism in tumor therapy with interferon is to stimulate cytotoxic T-lymphocytes to activate major histocompatibility complex antigens. Further, it is known that the interferon has immunity enhancement effects of stimulating natural killer cells and macrophages, shows endothelial cell proliferation and angiogenesis inhibitory effect, and has direct antiproliferative act on tumor cells.

Interferon is divided into three types such as alpha (α), beta (β), gamma (γ), wherein alpha (α) and beta (β) interferons are created in most of cells infected with the virus, and gamma (γ) interferon is synthesized only in T-lymphocytes and natural killer cells (NK cells).

According to an exemplary embodiment of the present invention, it may be confirmed that when the branched multi-peptide of the present invention is administered, a secretion capacity of the interferon gamma is remarkably increased, and it may be appreciated that the branched multi-peptide of the present invention may be effectively utilized for immunotherapy on tumors.

DETAILED DESCRIPTION OF MAIN ELEMENTS

TAA: tumor-associated antigen, tumor antigen
Multipeptide-cocktail: mixture of three single peptides of BIRC5 96 methionine, CD99 9, and ERBB2 369
Branched-multipeptide: branched peptide structure produced from three peptides of BIRC5 96 methionine, CD99 9, and ERBB2 369, using mini-PEG2
Branched DC-CTLs: cytotoxic lymphocytes produced through dendritic cells (DC) stimulated by branched multi-peptide
Unpulsed T2: T-lymphocyte in which peptide is not expressed
A,B,C T2: T-lymphocyte in which peptides of BIRC5 96 methionine, CD99 9, ERBB2 369 are separated and expressed in T2
A/B/C T2: T-lymphocyte in which peptides of BIRC5 96 methionine, CD99 9, ERBB2 369 are mixed and expressed in T2
Branched T2: T-lymphocyte in which branched multi-peptide is expressed in T2.
HIV T2: T-lymphocyte in which HIV is expressed

DETAILED DESCRIPTION OF EMBODIMENTS

Hereinafter, embodiments of the present invention will be described in detail with reference to the accompanying drawings. However, the detailed description is to help a specific understanding of the present invention, and the protection scope of the present invention is not limited to the following Examples.

[Chemical Material]
Spacer: mini-PEG2 (8-Amino-3,6-Dioxa-Octanoic acid)

Molecular Weight = 163.17
Molecular Formular = C6H13NO4

[Test Example 1] Screening of Tumor Antigen for Producing Multi-Peptide

Figure 1A:
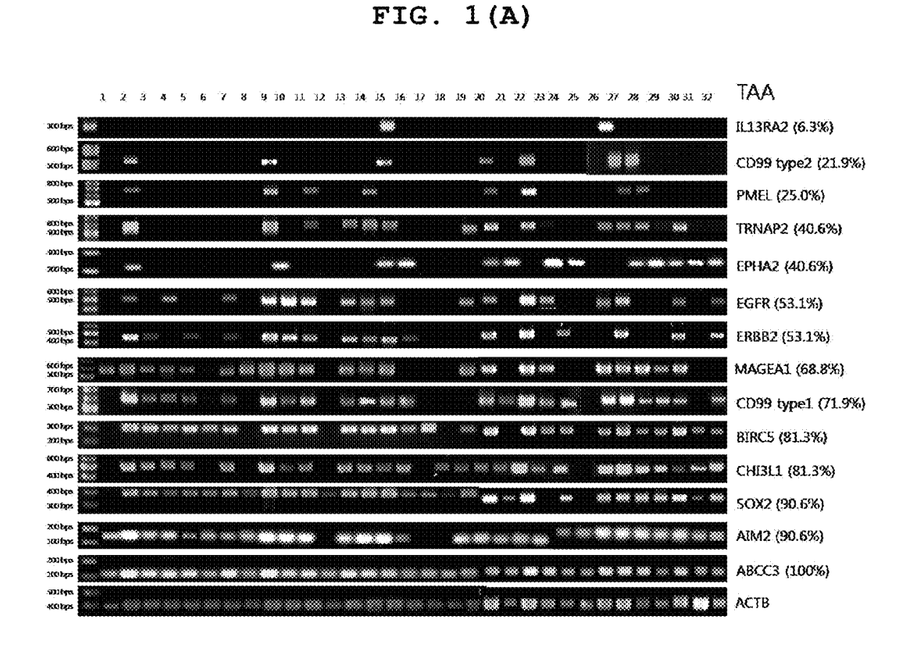
FIGS. 1(A) and 1(B) show expression aspects of tumor antigens from 32 glioblastoma tissues and from 7 normal brain tissues.
Figure 1B:
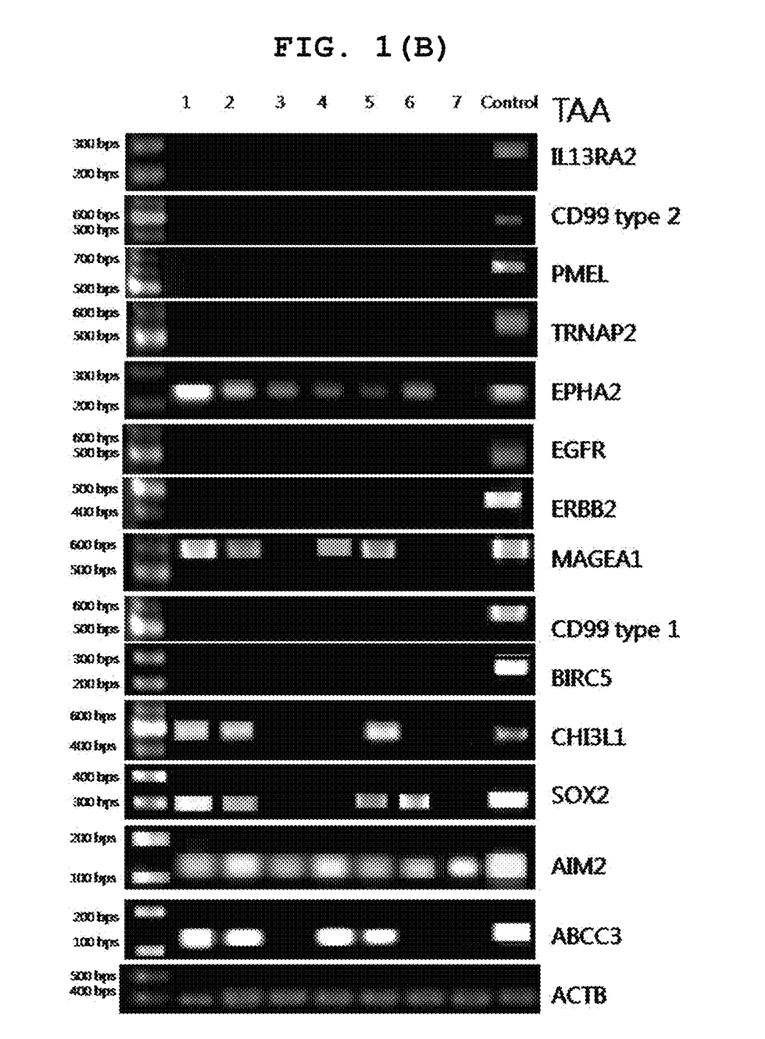
Figure 2:
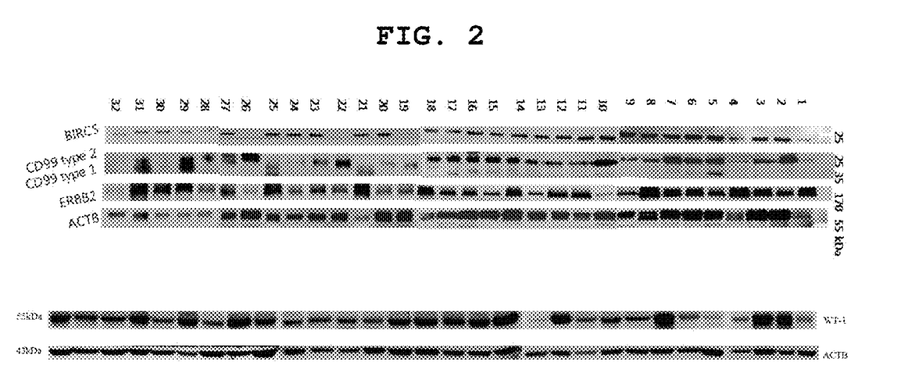
FIG. 2 shows screening of the tumor antigens expressed only in the glioblastoma tissues while not being expressed in the normal brain tissues.

Expression aspects of tumor antigens from 32 glioblastoma (one of malignant brain tumor) tissues and from 7 normal brain tissues were analyzed by general reverse transcription-polymerase chain reaction (RT-PCR) and western blot (FIG. 1). Among them, the tumor antigens expressed only in the glioblastoma tissues while not being expressed in the normal brain tissue were screened and used as a candidate tumor antigen for producing a multi-peptide (FIG. 2).

As a result after the screening, three antigens such as BIRC5, ERBB2 and CD99 satisfied the above conditions, and were used to produce the multi-peptide.

[Test Example 2] Measurement of Binding Capacity to T-Lymphocyte, of Each of the Subsequence Residues of Tumor Antigens for Synthesizing Multi-Peptide Relevant subsequence residues of the tumor antigens for synthesizing multi-peptide were summarized in Table 1 below.

TABLE 1

| Tumor antigen | SEQ ID NO: | Start position | Subsequence residue list |
|---|---|---|---|
| ERBB2 | 1 | 369 | KIFGSLAFL |
| ERBB2 | 2 | 106 | QLFEDNYAL |
| ERBB2 | 3 | 689 | RLLQETTELV |
| ERBB2 | 4 | 789 | CLTSTVQLV |
| ERBB2 | 5 | 63 | TYLPTNASL |
| BIRC5 | 6 | 5 | TLPPAWQPEL |
| BIRC5 | 7 | 95 | ELTGEFLKL |
| BIRC5 | 8 | 96 leucine | LLLGEFLKL |
| BIRC5 | 9 | 96 methionine | LMLGEFLKL |
| CD99 | 10 | 9 | LLLFGLLGV |
| CD99 | 11 | 6 | ALALLLFGL |
| CD99 | 12 | 13 | GLLGVLVAA |
| CD99 | 13 | 10 | LLFGLLGVL |
| WT-1 | 14 | 126 | RMFPNAPYL |
| WT-1 | 15 | 235 | CYTWNQMNL |
| WT-1 | 16 | 235 modified | CYTWNQMNL |
| PanDR epitope | 17 | — | aKXVAAWTLKAAaZC (X: cyclohexylalanine, Z: aminocarproic acid) |

Figure 3A:
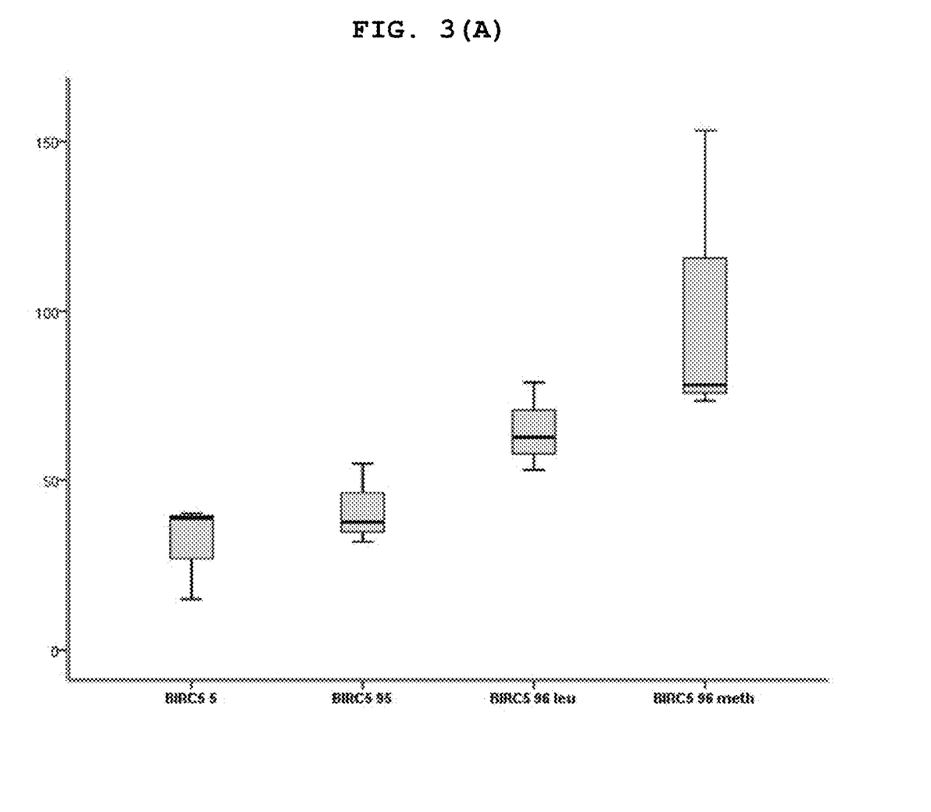
FIGS. 3(A), 3(B), and 3(C) show a binding capacity to T-lymphocyte, of each of the subsequence residues.
Figure 3B:
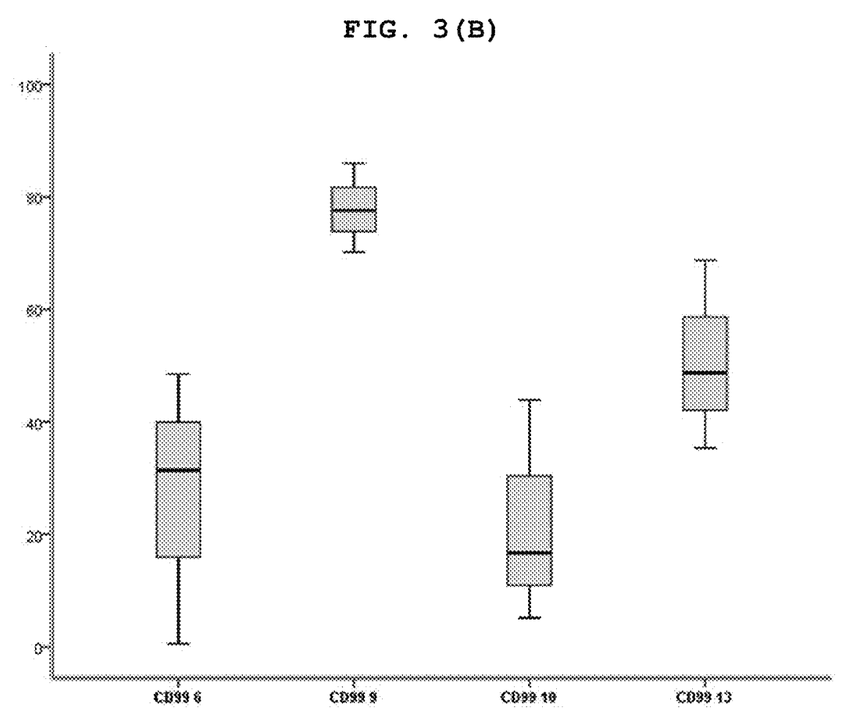
Figure 3C:
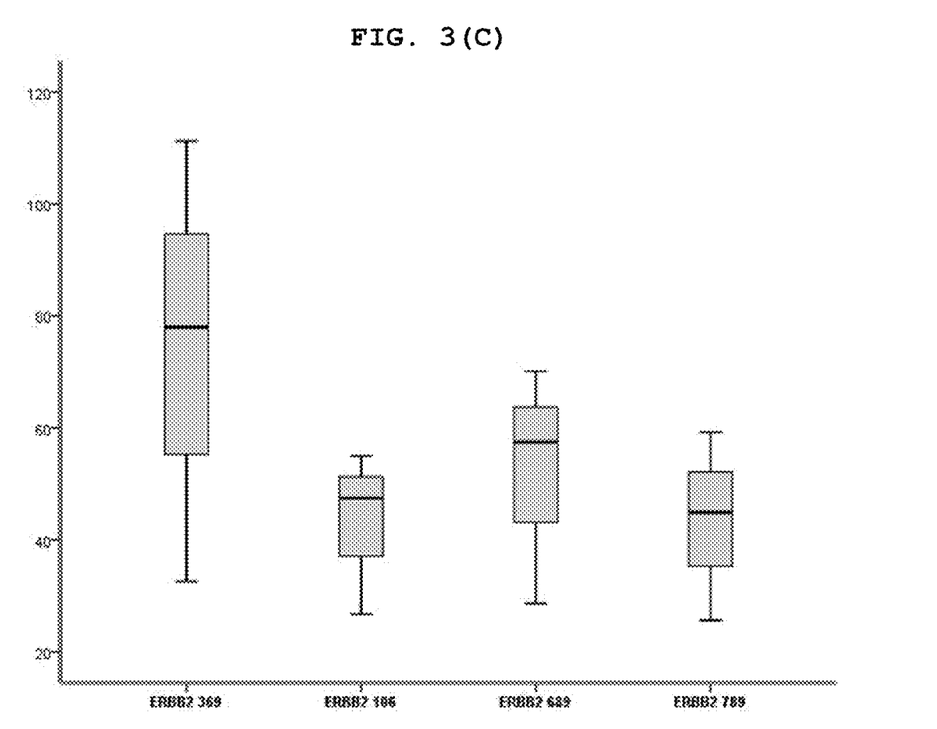

The binding capacity to T-lymphocyte, of each of the subsequence residues shown in Table 1 above, was measured (FIG. 3).

Measurement of binding capacity between T-lymphocyte and each of the subsequence residues T2 cell line (Korea Cell Line Bank) is a mixture of T cells and B cells expressing HLA-A2. The peptide and beta2-microglobulin on T2 cells were cultured overnight, and the T2 cells were stained with antihuman HLA-A2-FITCmAb, and analyzed by a FACS Caliber flow cytometer and WinMDI software.

The binding capacity of subsequence residue was calculated from mean fluorescence with the peptide and mean fluorescence without the peptide according to the following Equation:

$$\text{[Equation 1]} \quad \frac{\text{mean fluorescence with the peptide} - \text{mean fluorescence without the peptide}}{\text{mean fluorescence without the peptide}} \times 100$$

[Example] Synthesis of Branched Multi-Peptide

From the binding capacities measured by the above method and shown in FIG. 3, subsequence residues of ERBB2 of SEQ ID NO: 1, BIRC5 of SEQ ID NO: 9, and CD99 of SEQ ID NO: 10 each having the most excellent binding capacity, were selected. In addition, at the time of synthesizing a branched multi-peptide, mini-PEG2 (8-amino-3,6-dioxa-octanoic acid) was used as a spacer. Synthesis for the branched multi-peptide was performed by Peptron (37-24, Yuseong-daero 1628 beon-gil, Yuseong-gu, Daejeon, Korea).

A structure of the branched multi-peptide obtained by the synthesis is represented by the following Chemical Formula II:

branched multi-peptide and beta2-microglobulin on the T2 cells overnight, and treating the T2 cells with Brefeldin A. Then, the binding capacities were measured at each of 0, 2, 4, 8, and 24 hours to confirm the stability.

Figure 4:
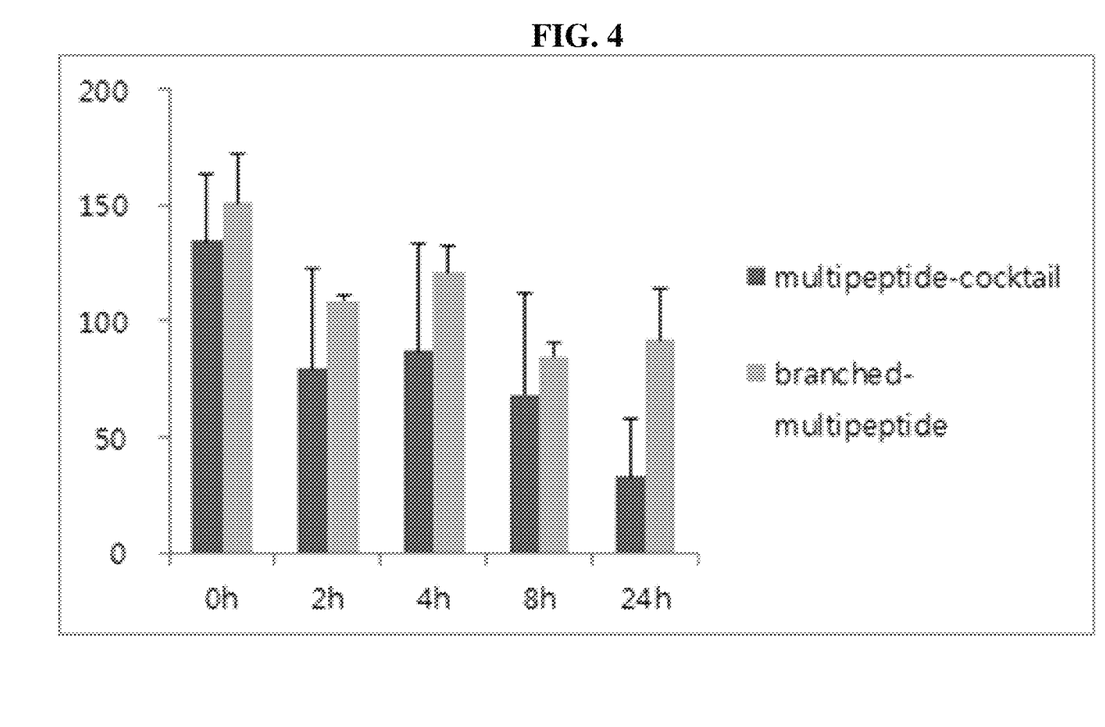
FIG. 4 shows a binding capacity to T-lymphocyte of branched multi-peptide, and stability after binding the branched multi-peptide.

For comparison with the measurement results of the binding capacity to T-lymphocyte of the branched multi-peptide synthesized by the above method, and stability after binding of the branched multi-peptide, mixture of oligopeptides (multipeptide-cocktail) each having subsequence residues of ERBB2 of SEQ ID NO: 1, BIRC5 of SEQ ID NO: 9, and CD99 of SEQ ID NO: 10, was set as a Comparative Example. The measurement results were compared between the multipeptide-cocktail and the branched multi-peptide. The results were shown in FIG. 4.

It was confirmed from the above results that as compared to the mixture of single oligopeptides, the binding capacity to T-lymphocyte of the branched multi-peptide was remarkably and stably maintained over time.

[Chemical Formula II]

[Test Example 3] Measurement of Binding Capacity to T-Lymphocyte of Branched Multi-Peptide, and Stability after Binding the Branched Multi-Peptide The binding capacity to T-lymphocyte and stability after binding, were measured on the branched multi-peptide having the structure of Chemical Formula II synthesized by above.

The binding capacity to T-lymphocyte of the branched multi-peptide was measured by culturing T2 cells with the produced branched multi-peptide and beta2-microglobulin overnight, and staining the T2 cells with antihuman HLA-A2-FITCmAb, and analyzing the T2 cells by a FACS Caliber flow cytometer and WinMDI software. Further, stability between T-lymphocyte and branched multi-peptide was measured by culturing T2 cells with the produced

[Test Example 4] Interferon Gamma Secretion Capacity of Cytotoxic T-Lymphocyte Stimulated with Branched Multi-Peptide Cytotoxic lymphocytes produced through dendritic cells (DC) stimulated by the above-produced branched multi-peptide were treated in T2 target cells each having compositions of Table 2 below.

TABLE 2

| Experimental Group | T-lymphocyte |
|---|---|
| 1 | T-lymphocyte in which peptide is not expressed |

TABLE 2-continued

| Experimental Group | T-lymphocyte |
|---|---|
| 2 | T-lymphocyte in which oligopeptides each having subsequence residues of ERBB2 of SEQ ID NO: 1, BIRC5 of SEQ ID NO: 9, and CD99 of SEQ ID NO: 10 are separately expressed in T2 |
| 3 | T-lymphocyte in which oligopeptides each having subsequence residue of ERBB2 of SEQ ID NO: 1, BIRC5 of SEQ ID NO: 9 and CD99 of SEQ ID NO: 10 are mixed and expressed in T2 |
| 4 | T-lymphocyte in which branched multi-peptide is expressed in T2 |
| 5 | T-lymphocyte in which HIV is expressed |

Measurement of the secretion capacity of interferon gamma-specific to each experimental group was performed by an enzyme-linked immunosorbent spot (ELISPOT, BD Biosciences). T-lymphocyte of each experimental group was a target cell and branched DC-CTLs (cytotoxic lymphocytes produced through dendritic cells (DC) with the branched multi-peptide as an antigen) were reaction cells. A ratio between the reaction cell and the target cell was 1:10, and the number of interferon-gamma was measured by an automatic CTL immunospot analyzer, and the data was expressed by Mean number of spots±standard deviation per $10^5$ $CD8^+$ T cells.

Figure 5:
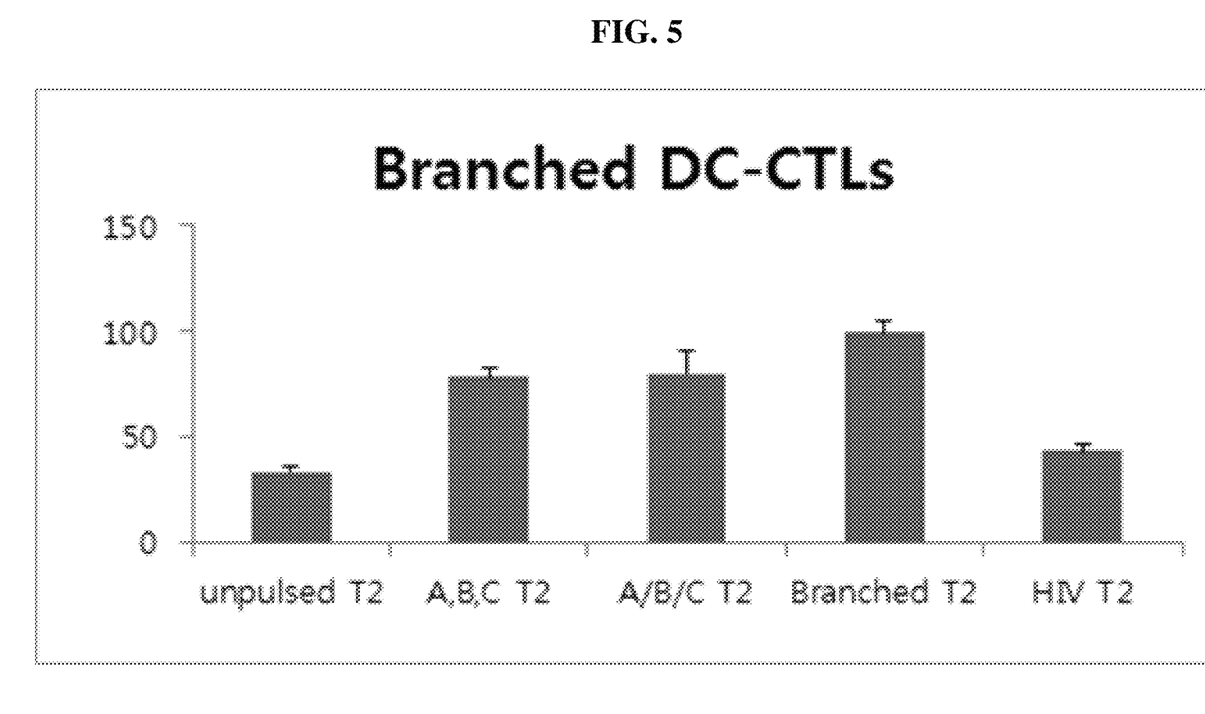
FIG. 5 shows interferon gamma secretion capacity of cytotoxic T-lymphocyte stimulated with branched multi-peptide.

The measurement results on each experimental group were shown in FIG. 5.

It could be confirmed from the above results that in the experimental group 2-4, the cytotoxic lymphocyte had largely increased secretion capacity of the interferon gamma, and particularly, the case of expressing the branched multi-peptide (Branched T2 in FIG. 5) had the largest increase of secretion capacity. Accordingly, it is expected that the branched multi-peptide vaccine according to the present invention is possible to be utilized as a vaccine for immunotherapy.

The branched multi-peptide vaccine according to the present invention is easy to be produced and utilized, thereby being easily applied to the treatment, and is capable of maintaining stable reaction in vivo, such that it is expected that the branched multi-peptide vaccine according to the present invention acts as an effective vaccine. Further, for the tumor antigen peptide, the present invention may select an antigen that is largely expressed in a malignant brain tumor. In addition, from now on, it is expected that tumor antigens having a large expression level may be analyzed depending on tumor characteristics of an individual patient, such that the branched multi-peptide vaccine according to the present invention may be utilized for producing personalized branched peptides and vaccines using the same.

What is claimed is:

1. A multi-peptide composition for cancer immunotherapy, represented by Chemical Formula I below:

$$A-Sp-Lys-Lys-Sp-C$$
$$|$$
$$Sp$$
$$|$$
$$B$$

Chemical Formula I in Chemical Formula I,
- each of A, B and C is independently a subsequence residue of any one brain tumor antigen selected from the group consisting of: CD99, BIRC5, ERBB2, WT-1 and PanDR epitope;
- Sp is a spacer that links the subsequence residue to lysine; and
- Lys is lysine,
- wherein A has any one amino acid sequence selected from SEQ ID NOs: 1 to 5, B has any one amino acid sequence selected from SEQ ID NOs: 6 to 9, and C has any one amino acid sequence selected from SEQ ID NOs: 10 to 13.

2. The multi-peptide composition for cancer immunotherapy of claim 1, wherein A has an amino acid sequence of SEQ ID NO: 1, B has an amino acid sequence of SEQ ID NO: 9, and C has an amino acid sequence of SEQ ID NO: 10.

3. The multi-peptide composition for cancer immunotherapy of claim 1, wherein Sp is 8-amino-3,6-dioxa-octanoic acid.

* * * * *